(12) United States Patent  
Pelletier et al.

(10) Patent No.: US 8,742,768 B1  
(45) Date of Patent: Jun. 3, 2014

(54) INTERROGATION MEASUREMENT SYSTEM AND METHOD PROVIDING ACCURATE PERMITTIVITY MEASUREMENTS VIA ULTRA-WIDEBAND REMOVAL OF SPURIOUS REFLECTORS

(75) Inventors: Mathew G. Pelletier, Idalou, TX (US); Joseph A. Viera, Jr., Manchester, NH (US); Gregory A. Holt, Brownfield, TX (US); John D. Wanjura, Lubbock, TX (US)

(73) Assignees: The United States of America as represented by the Secretary of Agriculture, Washington, DC (US); Microsemi Corporation, Alexandria, VA (US)

( * ) Notice: Subject to any disclaimer, the term of this patent is extended or adjusted under 35 U.S.C. 154(b) by 402 days.

(21) Appl. No.: 13/214,576

(22) Filed: Aug. 22, 2011

Related U.S. Application Data

(60) Provisional application No. 61/375,917, filed on Aug. 23, 2010.

(51) Int. Cl.  
*G01R 31/3193* (2006.01)

(52) U.S. Cl.  
USPC .......................................... 324/617; 324/71.1

(58) Field of Classification Search  
USPC ................................. 324/617, 71.1, 637, 639  
See application file for complete search history.

(56) References Cited

U.S. PATENT DOCUMENTS 7,135,871 B1 * 11/2006 Pelletier ........................ 324/640

* cited by examiner

*Primary Examiner* — Vincent Q Nguyen  
(74) *Attorney, Agent, or Firm* — John Fado; Randall E. Deck; Albert Y. Tsui

(57) ABSTRACT

A method and apparatus for determining at least one property of a target material is disclosed. The method is constituted of: providing a time varying signal at comprising frequency content over a range of frequencies; transducing the provided signal so as to interact with the target material; receiving the provided time varying signal after interaction with the target material; mixing the received time varying signal with a portion of the provided time varying signal; determining the propagation delay associated with the target material of the received provided time varying signal at each of a plurality of frequencies within the range of frequencies; and determining at least one property of the target material responsive to the determined propagation delay at each of the plurality of frequencies.

20 Claims, 13 Drawing Sheets

INTERROGATION MEASUREMENT SYSTEM AND METHOD PROVIDING ACCURATE PERMITTIVITY MEASUREMENTS VIA ULTRA-WIDEBAND REMOVAL OF SPURIOUS REFLECTORS

CROSS-REFERENCE TO RELATED APPLICATIONS

This application claims the benefit under 35 U.S.C. 1.19(e) of U.S. provisional 61/375,917 filed Aug. 23, 2010, the contents of which are incorporated by reference herein.

TECHNICAL FIELD

The present application relates to an apparatus and a method for obtaining material properties by substantially reducing impact of near proximity reflectors on the information obtained through interrogation of materials by wave energy.

BACKGROUND OF THE INVENTION

Utilization of electromagnetic energy for material characterization has found wide spread use and has a rich history. U.S. Pat. No. 2,659,860 issued Nov. 17, 1953 to Breazeale, teaches a method to measure the moisture content of bales of material, by directing a 10 GHz microwave beam through the bale and receiving the beam with another antenna on the far side of the bale from the one which generated the signal. The moisture content of the bale is then determined solely from the attenuation of this signal.

U.S. Pat. No. 4,361,801, issued Nov. 30, 1982 to Meyer and Schilz, teaches a sensing technique that requires measurements of both attenuation and the phase delay of propagation in order to calculate the real and the imaginary components of the complex permittivity measurement in order to measure moisture independent of density, utilizing a 9 GHz and higher microwave applicator. The basis for this measurement is the ratio of the real to the imaginary parts of the dielectric constant, followed by the application of a calibration curve for the specific material of the object. U.S. Pat. No. 6,147,503, issued Nov. 14, 2000 to Nelson et al., describes another moisture sensor algorithm that provides a moisture sensor that is independent of density over the narrow range of densities provided by loose seed kernel samples versus tightly packed seed kernel samples. They teach a technique that operates at 11.3 and 18 GHz similarly using both the attenuation and the propagation delay to calculate the complex permittivity of the material to derive an algorithm for the determination of the moisture content of the material. U.S. Pat. No. 6,476,619 issued Nov. 5, 2002 to Moshe et al., describes a microwave cavity perturbation technique for the sensing of moisture and or density in fibrous yarn, slivers or pad material that has a preferred operating range of 7 to 9 GHz. In the perturbation technique the system is setup with a resonant peak in the signal amplitude versus frequency plot and utilizes the frequency change in the location of this peak as the measure of permittivity change thereby providing a measure of the permittivity from which the moisture content can be estimated assuming a constant density of material. U.S. Pat. No. 6,111,415 issued Aug. 29, 2000 to Moshe, describes the use of a frequency modulated digital pulse of very high frequency microwaves for use as a density sensor. The attenuation and time delay of the signal are analyzed and corrected with empirically derived functions so as to calculate the moisture content and density of the material. Other patents by Moshe et al. include U.S. Pat. No. 5,845,529, issued Dec. 8, 1998, and U.S. Pat. No. 6,107,809, issued Aug. 22, 2000, which utilize a ratio of attenuation to phase delay measurement in a manner similar to the Meyer and Schilz U.S. Pat. No. 4,361,801, referenced above. The reccurring theme between all of these patents is that they all use very high microwave frequencies, typically above 7 GHz, and all of them utilize a measure of the attenuation of the signal after it has been transmitted through the material under test as the primary measure of the moisture content. It should be noted that the radar cross-section of the typical metal bale ties is very large at these high microwave frequencies and has been shown to cause significant signal interference at these very high frequencies, thereby rendering all of these frequencies unusable for use in moisture measurement of metal tied cotton bales. Additionally, these patents do not provide a general solution for measuring material property characteristics.

Given the evaluation of material properties is a fundamental operation for the control of processes and scientific investigations, it is not surprising to find these as well as other notable patents all looking to correlate material properties such as, without limitation, moisture and density, to the response of electromagnetic energy. Other notable references are: U.S. Pat. No. 4,135,131 issued Jan. 16, 1979 to Larsen et al; U.S. Pat. No. 5,256,978 issued Oct. 26, 1993 to Rose; U.S. Pat. No. 5,939,888 issued Aug. 17, 1999 to Nelson; U.S. Pat. No. 6,466,168 issued Oct. 15, 2002 to McEwan; U.S. Pat. No. 7,078,913 issued Jul. 18, 2006 to Pelletier; and U.S. Pat. No. 7,254,493 issued Aug. 7, 2007 to Pelletier, the entire contents of each of which are incorporated herein by reference.

Recently, the use of energy-wave based imaging is becoming more prevalent for detection of interior hidden material properties. In applications for detection of hidden moisture, microwave tomography can be used to image a cotton bale, or other material under test (MUT), and then perform an inverse calculation to derive an estimate of the variability of the hidden interior moisture, thereby alerting personnel to damaging levels of unseen moisture before degradation occurs. One impediment to this type of imaging is when near-by reflectors are too close to be filtered by conventional time-gating techniques, the reflectors divert off-axis energy back toward the receiving transducer which then create large deviations in measured signal propagation delays even though the material properties are uniform.

Other notable applications, of interest to science and industry, are for the determination of the time-varying soil moisture profile around a drip-line by means of the high correlation of soil moisture to the electromagnetic electrical permittivity, primarily responsive to the delay that occurs when an RF wave propagates through the soil. One proposed method of measuring this soil-moisture profile is to surround the drip-line with a series of antennas and have each antenna provide a straight path measurement, from transmitter to receiving transducer, of the permittivity of the material. Unfortunately, for many of the special case applications that perform close-proximity material measurements used in process control applications, there are typically strong reflectors in the same vicinity whose proximity is too close to utilize well known time-gating removal techniques for removal of unwanted reflectors from the desired direct-path measurement of propagation delay.

In the above referenced U.S. Pat. No. 6,466,168, McEwan teaches utilization of a time-domain radar system to measure the time-of-flight of an RF burst using differentially configured sampling receivers, so as to indicate antenna-to-antenna time-of-flight range or to indicate material properties. However there is no teaching regarding the RF pulse's relation to the bandwidth and/or to the relative wavelength ratios of the signal and the influence these parameters have on the received signal with respect to the desired direct path signal and the unwanted interfering multi-path signals that are due to scattering off of the local proximity neighboring off-axis reflectors, whereby said reflectors are both hard metallic reflectors as well as soft reflectors created by changes in material permittivities.

To date, significant work has been performed to utilize antenna arrays to infer the location of reflectors, however the prior art does not provide an accurate method utilizing only a single transmit and receiving antenna for measuring the desired direct-path propagation delay without interference, or with negligible interference, from close proximity off-axis neighboring reflectors.

SUMMARY

In view of the discussion provided above and other considerations, the present disclosure provides methods and apparatus to overcome some or all of the disadvantages of prior and present systems, apparatuses and methods for determining at least one property of a target material responsive to a wave source. Other new and useful advantages of the present methods and apparatus will also be described herein and can be appreciated by those skilled in the art.

In one embodiment a novel energy-wave based process and device is enabled for determination of an MUT's physical properties such as moisture or density of composition responsive to a multi-frequency method for removal of interference from neighboring reflectors, thus providing an accurate estimation of the direct-path propagation delay for the purpose of estimation of the aforementioned material properties and its use in the volumetric imaging of those properties.

Embodiments herein provide a novel technique for the removal of the scattered reflections from the direct-path signals, which thus enables material characterization via wave energy interrogations, including without limitation electromagnetic wave interrogations and acoustic wave interrogations. In particular, the material signal propagation delay (MSPD) is determined, which in certain embodiments is further correlated to physical material properties, such as electrical permittivity, which may be further correlated with other properties such as moisture content. In further detail, scattering is removed, or significantly attenuated, by obtaining measurements of the MSPD at multiple frequencies, and the obtained MSPD's are combined to arrive at a global MSPD characteristic of the target material substantially free of artifacts that are normally caused by off-axis reflected energy that interferes with the direct path wave energy of interest.

Certain embodiments enable an interrogation measurement circuit arranged to determine at least one property of a target material, the interrogation measurement circuit comprising: a frequency control functionality; at least one signal source responsive to the frequency control functionality and arranged to output a time varying signal comprising frequency content over a range of frequencies; a transducer in communication with the at least one signal source and arranged to output a first portion of the time varying signal so as to interact with the target material; a receiver arranged to receive the first portion of the time varying signal after interaction with the target material; a propagation delay calculation functionality arranged to determine the propagation delay of the received time varying signal at each of a plurality of frequencies over the range of frequencies; and a property determining functionality arranged to determine at least one property of the target material responsive to the determined propagation delay at each of the plurality of frequencies.

In one further embodiment the interrogation measurement circuit further comprises a mixer in communication with both the at least one signal source and the receiver, the mixer arranged to mix the received first portion of the time varying signal with a second portion of the time varying signal and output a mixed signal, the propagation delay calculation functionality responsive to the mixed signal. In one yet further embodiment a variable delay circuit is disposed between the at least one signal source and the mixer, the variable delay circuit responsive to the propagation delay calculation functionality, the propagation delay calculation functionality arranged to variably impose a delay on the second portion of the time varying signal between the at least one signal source and the mixer until a global delay match has occurred between the two signals at the mixer that are the delayed reference signal and the interrogation signal that was transmitted through the MUT whereby the delay of the reference signal, at the delay that provides the best match for all the frequencies that are interrogated thereby providing a global delay that is the desired measurement of delay of interest for the frequency span of interest.

In one further embodiment the range of frequencies is at least one-half of an octave. In another further embodiment the range of frequencies is at least one octave and preferably multiple octaves as the accuracy of the obtained measurement is improved as well as enhances the reduction of the off-axis reflected wave interferences.

In one further embodiment the at least one signal source comprises an adjustable-frequency signal source, and wherein the frequency content over the range of frequencies is supplied over a span of time. In another further embodiment the at least one signal source comprises a plurality of signal sources such that the interrogations at each frequency of interest occurs in parallel at one time, rather than being scanned.

In one further embodiment the at least one signal source comprises a plurality of signal sources, and wherein the frequency content over the range of frequencies is supplied simultaneously. In another further embodiment the at least one signal source comprises a swept frequency signal source, and wherein the frequency content over the range of frequencies is supplied over a span of time. In yet another further embodiment the at least one signal source comprises a pulsed signal exhibiting a rise time sufficient to provide the frequency content over the range of frequencies of interest spanning multiple octaves.

In one further embodiment the property is the permittivity. In another further embodiment an averaging functionality arranged to determine an average propagation delay of the received time varying signal over the range of frequencies is provided, the property determining functionality responsive to the determined average propagation delay. In another further embodiment the transducer is constituted of an antenna. In another further embodiment the transducer is a pressure wave generator.

Independently a method of determining at least one property of a target material is provided, the method comprising: providing a time varying signal comprising frequency content over a range of frequencies; transducing the provided signal so as to interact with the target material; receiving the provided time varying signal after interaction with the target material; determining the propagation delay associated with the target material of the received provided time varying signal at each of a plurality of frequencies within the range of frequencies; and determining at least one property of the target material responsive to the determined propagation delay at each of the plurality of frequencies.

In one further embodiment the method further comprises: mixing the received time varying signal with a portion of the provided time varying signal to provide a mixed signal, wherein the determining the propagation delay is responsive to the mixed signal. In another further embodiment the method further comprises variably delaying the portion of the provided time varying signal, wherein the mixing of the portion of the provided time varying signal is the variably delayed portion, and the determining of the propagation delay is responsive to the variably delaying.

In one further embodiment the range of frequencies is at least one-half of an octave. In another further embodiment the range of frequencies is at least one octave.

In one further embodiment the frequency content over the range of frequencies is supplied over a span of time. In another further embodiment the frequency content over the range of frequencies is supplied simultaneously.

In one further embodiment the frequency content is swept over the range of frequencies. In another further embodiment the provided time varying signal is a pulsed signal exhibiting a rise time sufficient to provide the frequency content over the range of frequencies.

In one further embodiment the property is the permittivity. In another further embodiment the method further comprises averaging the determined propagation delays to determine an average propagation delay, wherein the determining at least one property is responsive to the determined average propagation delay.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF PREFERRED EMBODIMENTS

Figure 1A:
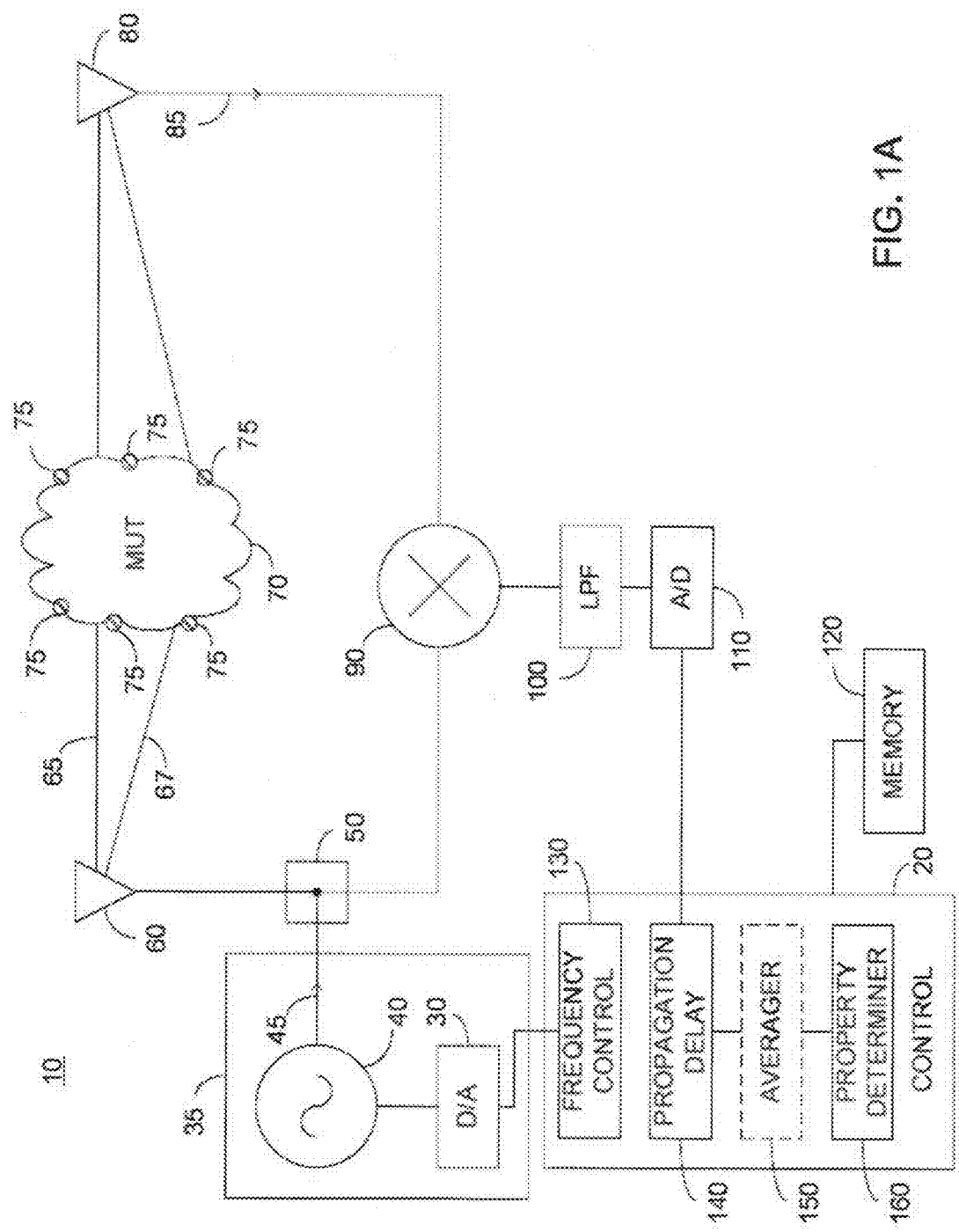
FIG. 1A illustrates a high level block diagram of an exemplary embodiment of an interrogation measurement circuit arranged to measure permittivity of an MUT subject to local proximity reflectors, the system comprising a single adjustable-frequency continuous-wave signal source.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

In the practical application of material sensing in free-space, certain embodiments enabled herein utilize transmission of electromagnetic energy that is unconstrained through by means of transmission. In the aforementioned free-space transmission of wave energy, a transducer, such as an antenna, is utilized to couple the energy from the signal generator to free-space. The signal, in making this transition to free-space, radiates a significant portion of the energy exiting the antenna into off-axis directions, away from the desired direct path that runs from the transmitting to the receiving antenna. This off-axis energy is free to scatter off of neighboring reflectors which then redirect the off-axis energy back towards the receiving antenna to be then combined with the direct path signal, thereby degrading the accuracy of the measurement. A similar result occurs for other wave applications such as acoustic waves.

In large distance radar applications, there have been developed several techniques for removing this scatter utilizing both time and frequency gating. Unfortunately, due to the very close proximity of the reflectors in many practical applications for material sensing, neither time nor frequency gating are feasible as the separation in time or frequency is too small to achieve the requisite separation. Embodiments herein provide an alternative technique for the removal of the scattered reflections from the direct-path signals, which thus enables material characterization via wave energy interrogations, including without limitation electromagnetic wave interrogations and acoustic wave interrogations. In particular, the material signal propagation delay (MSPD) is determined, which in certain embodiments if further correlated to physical material properties, such as electrical permittivity, which may be further correlated with other properties such as moisture content. In further detail, scattering is removed by obtaining measurements of the MSPD at multiple frequencies, and the obtained MSPD is combined to arrive at a global MSPD characteristic of the target material.

The below embodiments are detailed in relation to a microwave electromagnetic system arranged to detect moisture content of baled cotton, however this is not meant to be limiting in any way. The teachings herein are equally applicable to any parameters of a target object which affects the propagation delay of a time varying signal. The teachings herein are equally applicable to any range of electromagnetic radiation, and to acoustic waves, without limitation.

It is noted that the most applicable application of this process and device is for the case whereby said neighboring reflectors are too close in proximity to remove the reflected energy, hereafter known as multipath signals, by other conventional means such as time or frequency gating, such as was taught in the above referenced U.S. Pat. No. 7,078,913, however other advantageous applications are contemplated. Advantageously, certain embodiments herein allow for electronic removal of these multipath signals from the measured signal.

Figure 5:
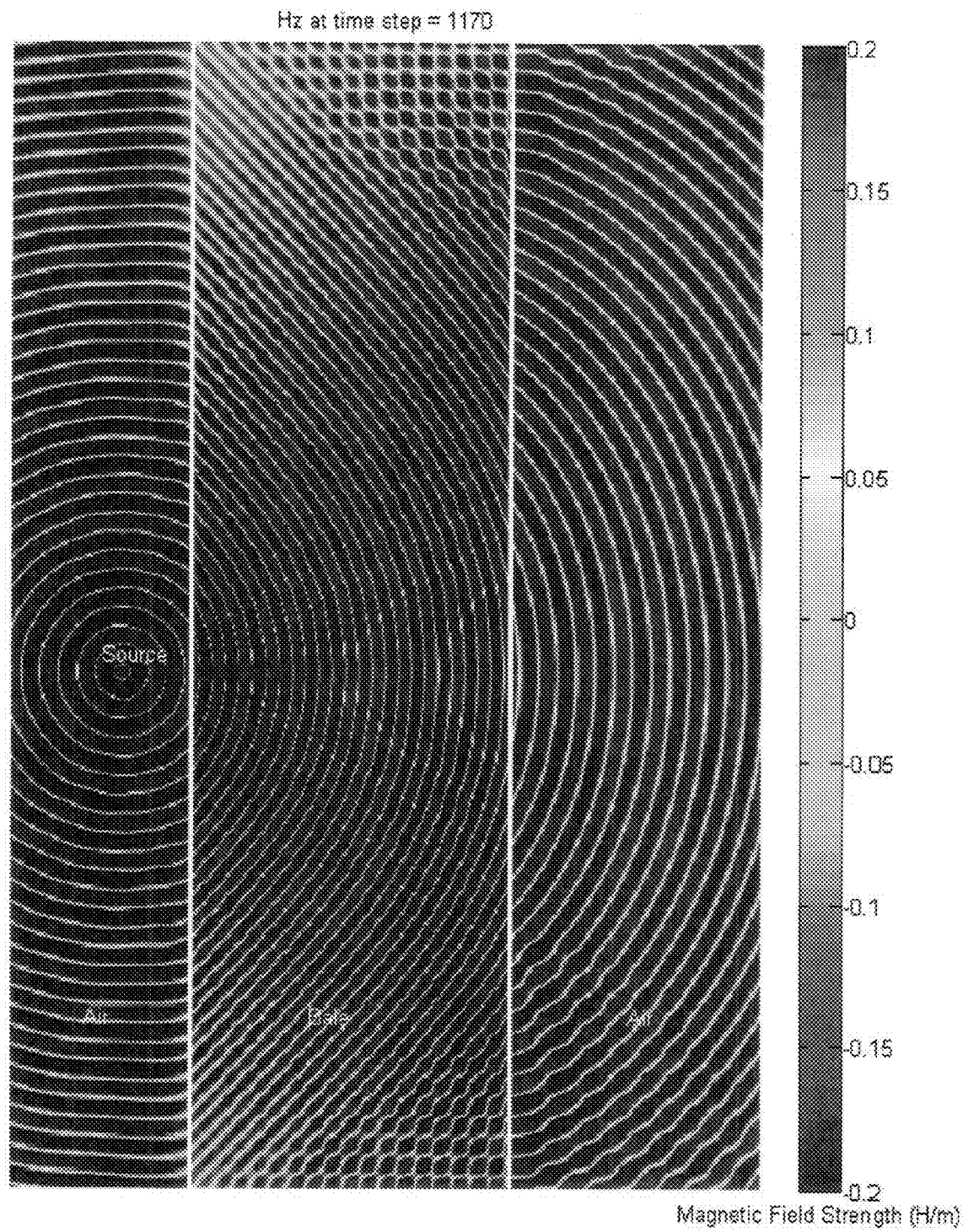
FIG. 5 illustrates a finite difference time-domain model simulation showing signal propagation without interference from local proximity reflectors.
Figure 6:
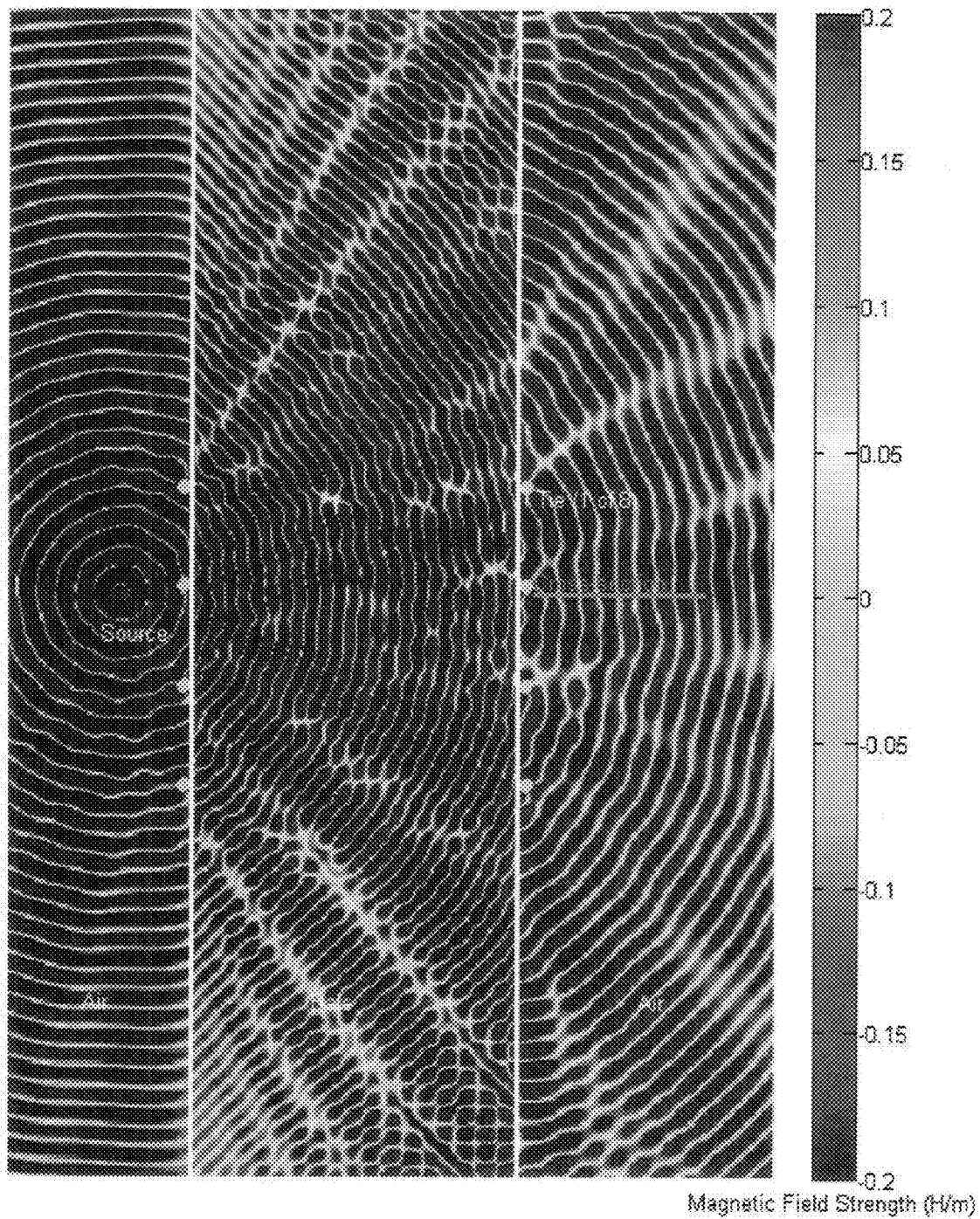
FIG. 6 illustrates a finite difference time-domain model simulation showing signal propagation with interference from local proximity reflectors.
Figure 7:
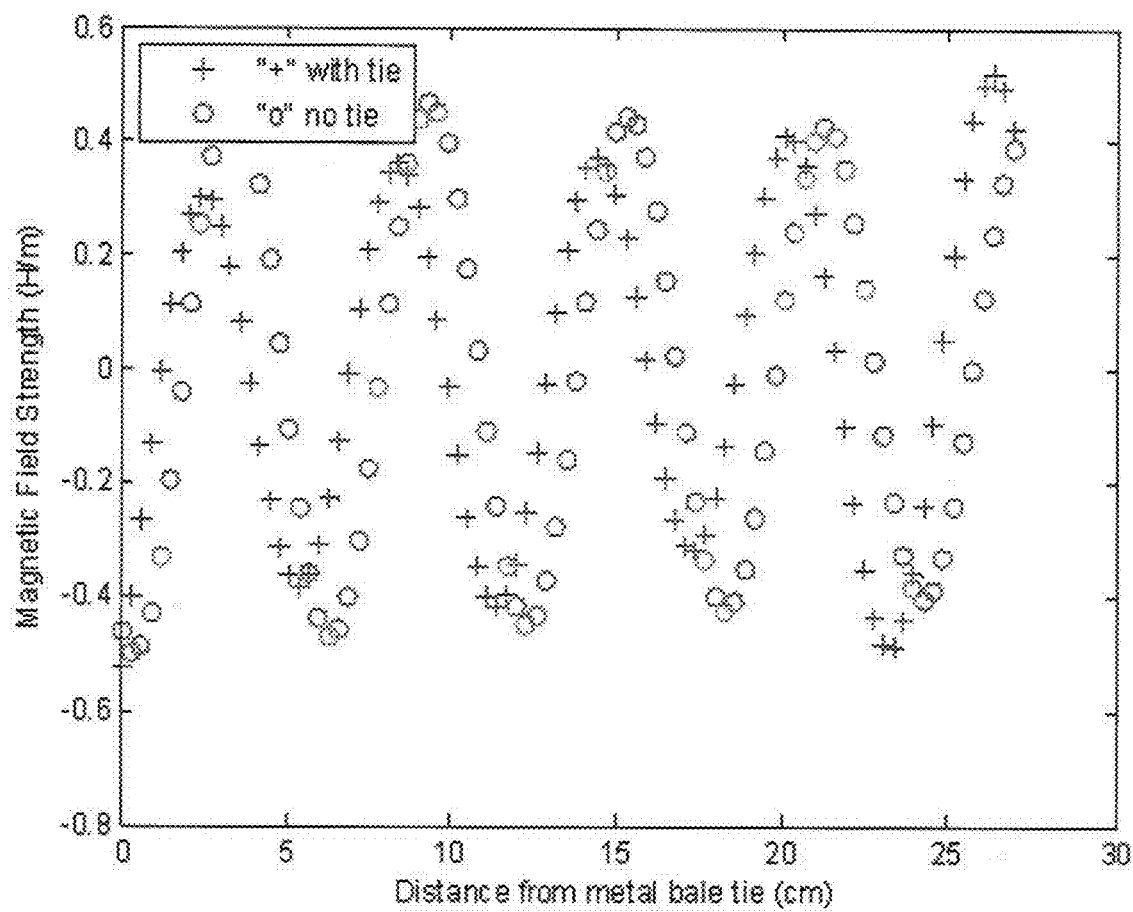
FIG. 7 illustrates the magnetic field force versus distance for each of the simulations of FIG. 5 and FIG. 6.
Figure 8:
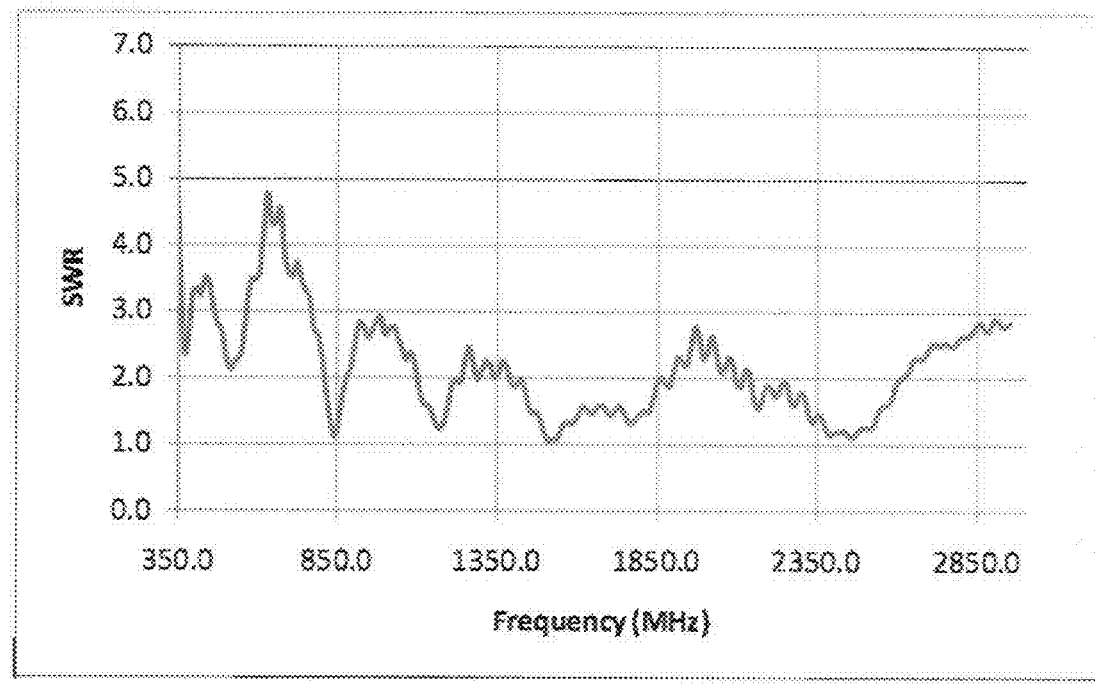
FIG. 8 illustrates a plot of the SWR vs. bandwidth performance of the antennas.

To further illustrate the issues associated with close proximity reflectors on the desired direct-path signals, a finite-difference time-domain simulation model was developed to study the issues. FIG. 5 details the results of a simulation that shows how a direct path signal proceeding from right to left, without close proximity reflectors, provides a very clean signal to be picked up at the far side of an MUT for determination of the physical properties of the MUT, such as density or moisture content, wherein the magnetic field strength in H/m is encoded by the various colors as indicated in the reference bar to the right. The radiator of the electromagnetic signal is at the extreme left pane, and the electromagnetic signal is radiated in air. To the immediate right of the air portion is a uniform cotton bale being the MUT, and to the immediate right of the uniform cotton bale is an additional air portion. FIG. 6 is the dual simulation to FIG. 5 including close proximity reflectors which do in fact create significant ripples in the propagating waves, the close proximity reflectors comprise wire ties at predetermined points about the cotton bale MUT. Of particular interest is the fact that both the near and the far side reflectors influence the wave propagation and the recovered signal at the far side of the MUT. Using the cross-sectional area depicted in each of FIG. 5 and FIG. 6, the signal propagation between the clean case, without reflectors, can be compared to the case with interfering reflectors. The results of the comparison are plotted in FIG. 7, where the x-axis depicts distance in centimeters from the plane aligned along the line of the close proximity reflectors, i.e. the wire ties, and the y-axis reflects magnetic field strength. The plot points for the depiction of FIG. 5 without ties are depicted with a circle (o) and the plot points for the depiction of FIG. 6 with ties are depicted with a plus (+). As is readily apparent from the plots, a significant amount of phase and amplitude distortion is created by the presence of the ties.

Figure 9:
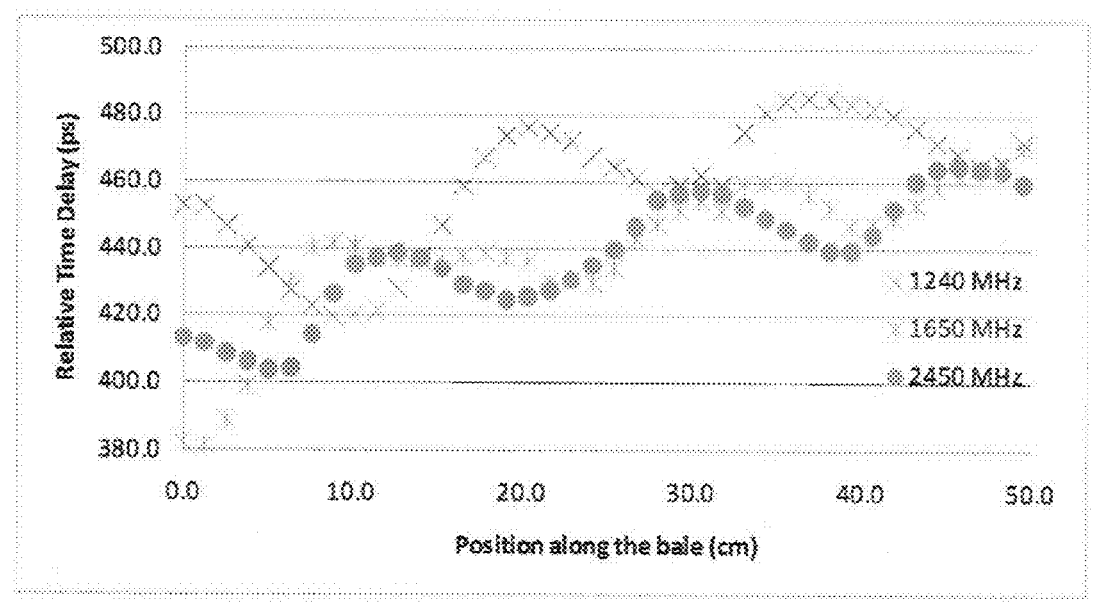
FIG. 9 illustrates a plot of the relative time delay for signals proceeding from the transmitting antenna to the receiving antenna as a function of position along a test MUT, particularly a cotton bale with wire ties, for each of a plurality of frequencies.

Further testing was performed utilizing the experimental configuration, where a typical commercially packaged cotton bale tied with metal bale ties was placed on a conveyor for precise positioning with respect to the antenna placements. The near proximity metal tie reflectors create the interference and provide significant errors in the estimation of material properties with the x-axis and y-axis both measured in millimeters. The experiment was conducted utilizing a bale that was conditioned to a uniform moisture content with a slight taper in density to provide a slow gradient from the leading edge to the trailing edge of the bale, which in this configuration should provide a slight slope to the measured material properties as the bale is scanned past the antennas. As can be seen by FIG. 9, wherein the x-axis depicts position along the cotton bale in centimeters, the y-axis depicts relative time delay of the signal in picoseconds, and various frequencies of the signals are plotted, particularly 1240 MHz depicted with "x", 1650 MHz depicted with a star and 2450 MHz depicted with a dot, the near proximity wire reflectors create significant distortion to the measurement with a periodicity that matches the spacing on the wire ties, but with the phase of this periodicity affected by the particular interrogation frequency. Thus, due to the unknown frequency interaction with the wire ties, the distortion is difficult to predict or remove through conventional filtering means.

EXAMPLE 1

FIG. 1A illustrates a high level block diagram of an exemplary embodiment of an interrogation measurement circuit 10 arranged to measure permittivity of an MUT 70 subject to close proximity reflectors 75, the system comprising a single adjustable-frequency time varying signal source 35, illustrated without limitation as a continuous-wave (CW) source. In particular, interrogation measurement circuit 10 comprises: a control circuitry 20; adjustable-frequency continuous-wave signal source 35 constituted of a digital to analog (D/A) converter 30 and a voltage controlled oscillator (VCO) 40 arranged to output a time varying signal 45 whose frequency is responsive to an output of D/A converter 30; a signal splitter 50; a transmitting transducer, illustrated without limitation as a transmit antenna 60; a direct path signal 65; an off-axis path signal 67; a receiving transducer, illustrated without limitation as a receive antenna 80 arranged to receive direct path signal 65 after interaction with MUT 70 and to further receive a portion of off-axis path signal 67 after interaction with MUT 70 and close proximity reflectors 75; a mixer 90; a low pass filter 100; an analog to digital converter (A/D) 110; and a memory 120. Control circuitry 20 comprises: a frequency control functionality 130; a propagation delay determining functionality 140; an optional averaging functionality 150, illustrated with a broken line; and a property determining functionality 160. The combination of D/A converter 30 and VCO 40 provides for an adjustable-frequency continuous-wave signal source 35 responsive to frequency control functionality 130. Control circuitry 20 may be constituted of a general purpose processor running machine readable instructions stored on memory 120, or as dedicated hardware without limitation. Each of frequency control functionality 130, propagation delay determining functionality 140, optional averaging functionality 150 and property determining functionality 160 may be constituted of machine readable instructions stored on memory 120 or alternatively as dedicated hardware without limitation. Mixer 90 is preferably constituted of a frequency mixer, also known as a signal multiplier, arranged to output a mixture of signals at several frequencies, including without limitation: a signal whose frequency is the sum of the frequencies of the input signals; and a signal whose frequency is the difference between the input signals.

The output of control circuitry 20, particularly associated with frequency control functionality 130, is connected to an input of D/A converter 30, and the output of D/A converter 30 is connected to the control input of VCO 40. Output time varying signal 45 of VCO 40 is connected to the input of signal splitter 50, and a first output of signal splitter 50 is connected to a first input of mixer 90 and a second output of signal splitter 50 is connected to the input of transmit antenna 60. Transmit antenna 60 is preferably a wide band antenna arranged to provide acceptable performance over at least ½ octave, i.e. from a minimal frequency to 1.5 times the minimal frequency, and preferably at least one octave.

Transmit antenna 60 outputs direct path signal 65 which propagates along a direct path from transmit antenna 60 to receive antenna 80 via MUT 70, and is thus received at receive antenna 80 after interaction with MUT 70. Transmit antenna 60 additionally outputs off-axis path signal 67 which interacts with at least one of close proximity reflectors 75 and optionally a portion of MUT 70 and at least a portion of which propagates to receive antenna 80. Receive antenna 80, comprising therein any required amplification, outputs a signal 85 representing a combination of the received direct path signal 65 after interaction with MUT 70 and off-axis path signal 67 after interaction with MUT 70 and close proximity reflectors 75. Signal 85 is connected to the second input of mixer 90.

The output of mixer 90 is connected to the input of low pass filter 100, and the output of low pass filter 100 is connected to the input of A/D converter 110. The output of A/D converter 110 is connected to the input of control circuitry 20, particularly to the input of propagation delay determining functionality 140. Propagation delay determining functionality 140 is in communication with optional averaging functionality 150, and optional averaging functionality 150 is in communication with property determining functionality 160. Control circuitry 20 is further in communication with memory 120.

Figure 1B:
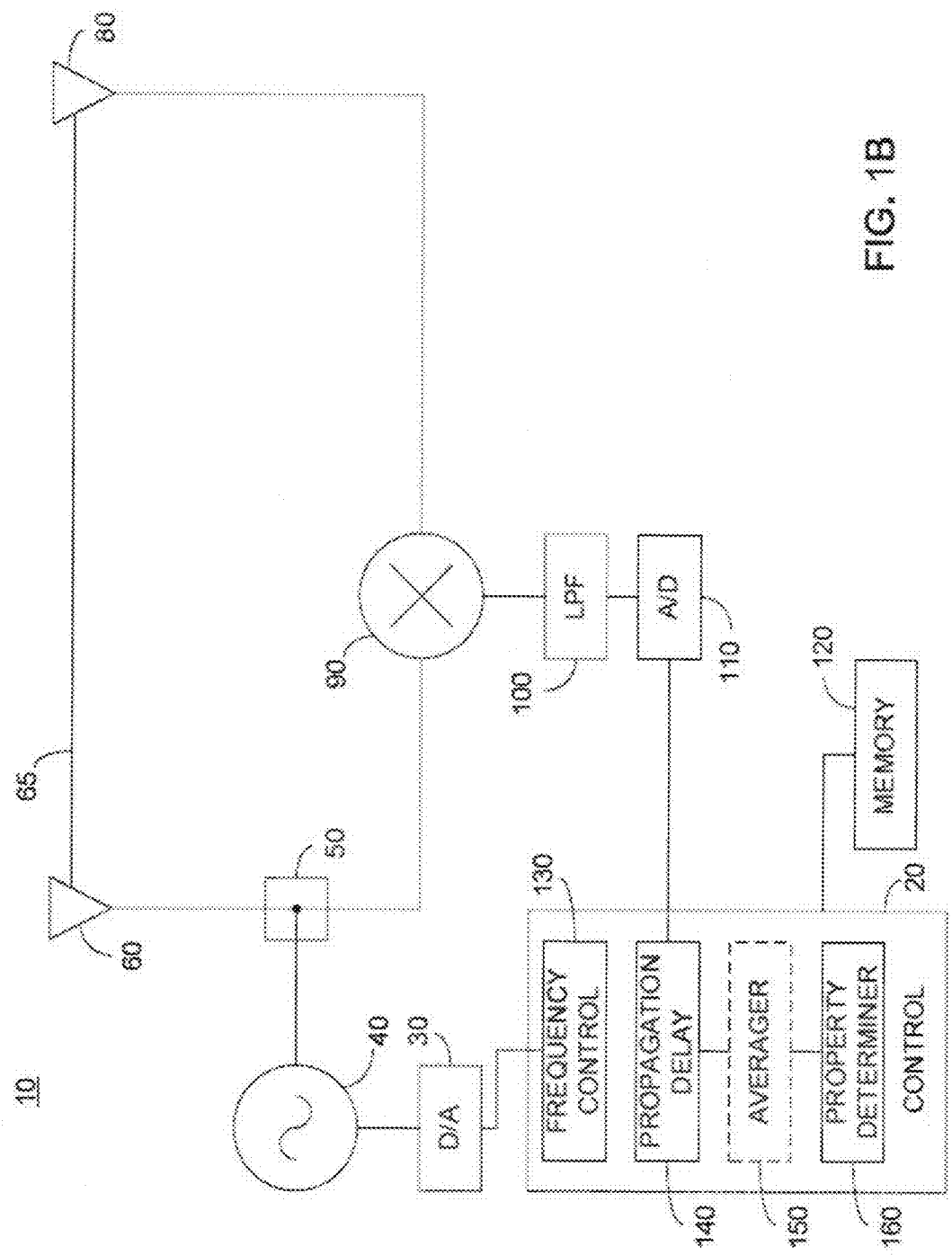
FIG. 1B illustrates a high level block diagram of the interrogation measurement circuit of FIG. 1A without the MUT thus arranged to provide a reference for use in calibration of permittivity.
Figure 1C:
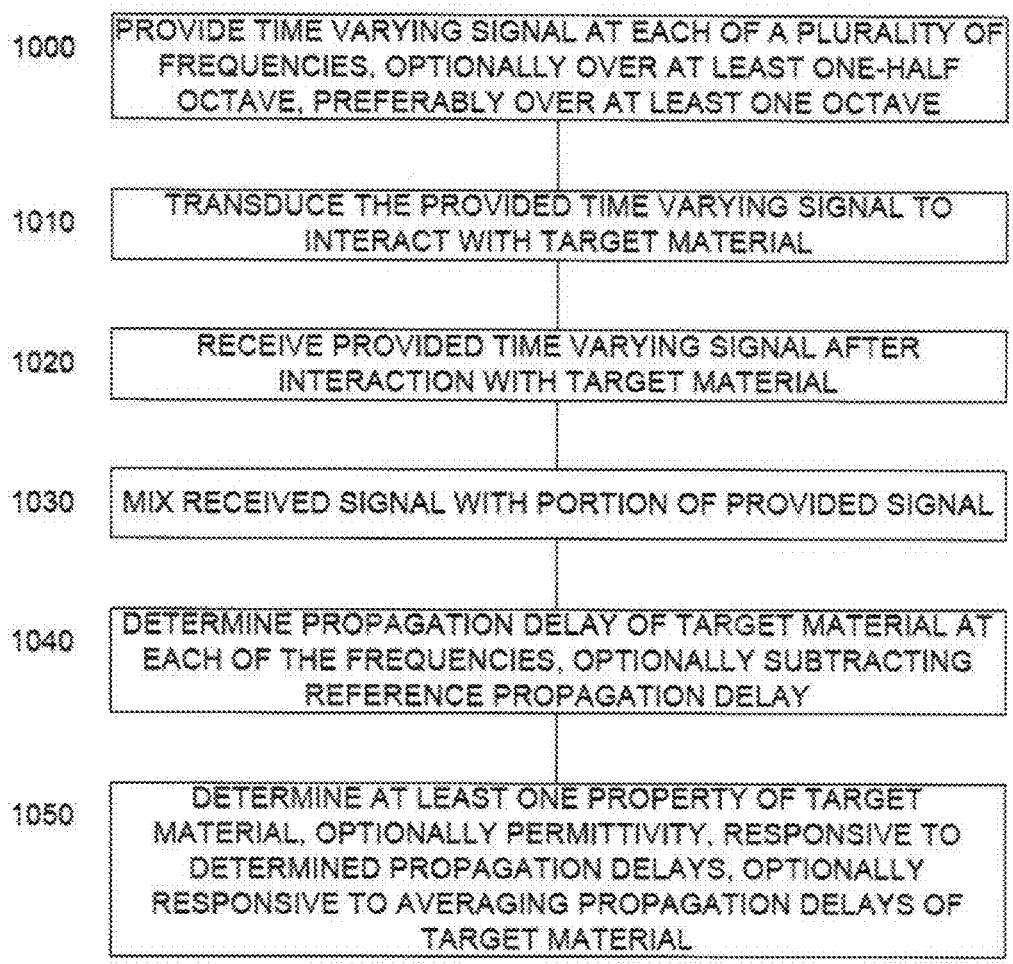
FIG. 1C illustrates a high level of flow chart of the method of operation of the interrogation measurement circuit of FIG. 1A.

FIG. 1B illustrates interrogation measurement circuit 10 of FIG. 1A with MUT 70 and the associated close proximity reflectors 75 removed, thus only direct path signal 65 is present. FIG. 1C illustrates a high level of flow chart of the method of operation of the system of FIG. 1A. For clarity and ease of understanding FIGS. 1A-1C will be described together.

In operation, as described in stage 1000, frequency control functionality 130 is arranged to control VCO 40 to produce a time varying signal at each of a plurality of frequencies, optionally the plurality of frequencies range over at least one half octave, i.e. the highest frequency is at least 1.5 times greater than the lowest frequency, and preferably the plurality of frequencies range over at least one complete octave. It is to be understood that such a limitation, if implemented, is relevant to the selection criteria for both transmit antenna 60 and receive antenna 80. In one embodiment the frequencies are varied in steps of ⅛ wavelength, i.e. the wavelength of each subsequent measurement is perturbed ⅛ wavelength from the previous measurement. Preferably the bandwidth is limited in the case of electromagnetic radiation so that the cross section of MUT 70 which passed electromagnetic radiation to receive antenna 80 lies within the Mie scattering region. Further preferably, the wavelength of frequencies utilized should exhibit a wavelength more than 1.5 times the spacing between adjacent close proximity reflectors 75. In another embodiment the frequencies are varied in steps of ¼ wavelength, and in yet another embodiment the frequencies are varied in steps of ½ wavelength. In one particular embodiment, frequency control functionality 130 outputs a digital control word representation of each of the plurality of frequencies, and D/A converter 30 is operative to convert the digital control word to an analog voltage which controls the frequency of time varying signal 45 output by VCO 40. In one non-limiting embodiment, particularly relevant to determining at least one parameter of baled cotton, the frequency of time varying signal 45 is a microwave frequency of 300 MHz to 2850 MHz.

Time varying signal 45 is received by signal splitter 50, arranged to provide a first portion of time varying signal 45 to transmit antenna 60 and to provide a second portion of time varying signal 45 to mixer 90. As described at stage 1010, transmit antenna 60 transduces the received time varying signal 45 to free space electromagnetic radiation, a first portion of which propagates as direct path signal 65 through MUT 70 to receive antenna 80 and a second portion of which propagates as off-axis path signal 67 through MUT 70 and close proximity reflectors 75 to receive antenna 80. Off-axis path signal 67 is at least partially responsive to the location, size, material, and spacing of the various close proximity reflectors 75. There is no limitation to the propagation path of the free space electromagnetic radiation exiting transmit antenna 60, and a plurality of off-axis path signals 67 may exist without limitation. Additionally, off-axis path signals may exist which do not interact with MUT 70, and furthermore a portion of the electromagnetic radiation exiting transmit antenna 60 may not be received by receive antenna 80, without limitation. Transmit antenna 60 and receive antenna 80 are illustrated as being on opposing sides of MUT 70, however this is not meant to be limiting in any way, and in another embodiment transmit antenna 60 is collocated with receive antenna 80. In one particular embodiment, a single time shared antenna is provided for both transmit antenna 60 and receive antenna 80.

The time of travel of the portion of free space electromagnetic radiation propagating through MUT 70 is affected by the properties of MUT 70. In particular, the propagation velocity through MUT 70 is a function of the electrical permittivity of the constituent material of MUT 70.

As described above, and as indicated at stage 1020, receive antenna 80 captures energy from both direct path signal 65 and off-axis path signal 67 after interaction with MUT 70, and outputs the combined signal energy as signal 85. Mixer 90 receives signal 85 and, as described at stage 1030, mixes signal 85 with the provided portion of time varying signal 45 of stage 1000. It is to be noted that the received signal of stage 1020 and the provided signal portion of stage 1030 are of the same frequency, with a phase difference at least partially reflective of the permittivity of MUT 70. Low pass filter 100 is arranged to strip the high frequency portion of the output of mixer 90, thus passing only the difference signal to A/D converter 110, which digitizes the difference signal for provision to propagation delay determining functionality 140.

Propagation delay determining functionality 140 is arranged, as described at stage 1040, to determine the propagation delay associated with MUT 70 at each of the plurality of frequencies of stage 1000, by converting the phase delay of the signal received from A/D converter 110 at the frequency of stage 1000 to a time delay, or frequency independent phase component Beta of the propagation constant. In an exemplary embodiment, as illustrated in FIG. 1B, stages 1000-1030 are performed at each frequency in the absence of MUT 70 and the associated close proximity reflectors 75, to determine a reference propagation delay for interrogation measurement circuit 10. The reference propagation delay is preferably stored, associated with the frequency, in memory 120, and deducted from the determined propagation delay. Deducting the reference propagation delay thus removes the influence of any internal reflections and delays. Alternatively, a delay line may be provided between splitter 50 and the first input of mixer 90 simulating the internal delay of interrogation measurement circuit 10, so that the propagation delay determined by propagation delay determining functionality 140 is inherently adjusted for any internal delay of interrogation measurement circuit 10. In particular, propagation delay determining functionality 140 determines the relative phase delay of the signal received at receive antenna 80. It is to be noted that the phase delay determined is an unwrapped value, i.e. the values are not constrained to be within 360°.

In some further detail, transmission from transmit antenna 60 to receive antenna 80 exhibits a transmission path length irrespective of the existence or absence of MUT 70, which inherently adds some phase delay to be accounted for. Thus, the transmission path length impacts the measurement, and knowledge of the transmission path length is preferred in order to calculate permittivity of material, or the Beta delay, also known as the phase constant, in accordance with:

$$\gamma = jk = \alpha + j\beta = j\sqrt{\varpi^2\mu\left(\varepsilon' - j\frac{\sigma}{\varpi} - j\varepsilon''\right)} = j\sqrt{\varpi^2\mu\varepsilon'(1 - j\tan\delta)}$$

where
γ=propagation constant for the medium;
α=attenuation constant for the medium (N/m); and
β=phase constant for the medium (rads/m) which is a measure of propagation delay;
∈'=real portion of complex permittivity (F/m), which also represents delay;
∈"=imaginary portion of complex permittivity (F/m), which represents attenuation due to dielectric damping;
σ=conductivity (S/m), which also very low frequency or DC loss;
μ=permeability of material (H/m);
ω=oscillation rate which is equal to 2 pi*frequency (rads/sec);
j=sqrt(-1), imaginary term.

Thus, the output of propagation delay determining functionality 140 exhibits the propagation delay of the signal caused by MUT 70 and further a portion of the propagation delay attributable to the various close proximity reflectors 75.

Property determining functionality 160, optionally in cooperation with optional averaging functionality 150, as described in stage 1050, is arranged to determine at least one property of MUT 70 responsive to the propagation delays output by propagation delay determining functionality 140 of stage 1040. Suitable propagation delay determining functionality can be provided, but not limited to that provided by; digital xor gate, analog mixer such as a Gilbert multiplier, single balanced mixer as known in the radio frequency art, similiarly the double balance mixer, a simple diode when operated in the non-linear region, back to back mosfets arranged to provide mixing functionality as well as other similar analog of digital circuits known in the state of the art. Propagation delay determining functionality can also be provided by means of mathematical analytical analysis of the digitized signals through correlation functions. In one embodiment, a global propagation delay is determined from an average propagation delay by combining propagation delay measurements, from measurements at each frequency, across the range of frequencies of stage 1000 is determined, the global propagation delay, or average propagation delay, representing an improved approximation of the actual propagation delay of MUT 70. In particular the effect of the various close proximity reflectors 75 cancel out, and thus the average value over the range of frequencies provides a measure of the propagation delay of MUT 70 substantially independent of the off-axis scattered interference. The propagation delay of MUT 70 is a function of the permittivity, and thus permittivity of MUT 70 may be directly obtained. Preferably, the global propagation delay is determined with appropriate frequency weighting, since in many instances not all frequencies enjoy the same signal strength, thus utilization of a statistical based weighting is preferred to minimize contributions from frequencies that are subjected to a weaker strength signal and higher noise leading to a reduction in the signal to noise ratio wherein the cause of weaker strength could be due to impedance miss-matches on antennas, extreme multi-path interferences or simply interference from other transmitter operating in the vicinity. One example of such an improved weighting could be based upon an optimal statistical characterization that seeks to minimize the noise either by Newton's method or one that seeks to minimize the mean-square error by following a gradient descent across the performance surface utilizing a criterion function that is designed to characterize and minimize the signal noise. The weighting functions could be performed either statically through an optimal Weiner analysis or dynamically in an adaptive type algorithm such as an adaptive LMS or Least-Squares analysis that is performed continuously during operation. Examples known in the state of the art, but not limited to, are from the text book "Adaptive Signal Processing" by Bernard Widrow and Samual D. Stearns published by Prentice-Hall Inc. Englewood Cliffs, N.J. 07632 copyright 1985, ISBN 0-13-004029, referenced herein in its entirety.

Figure 10:
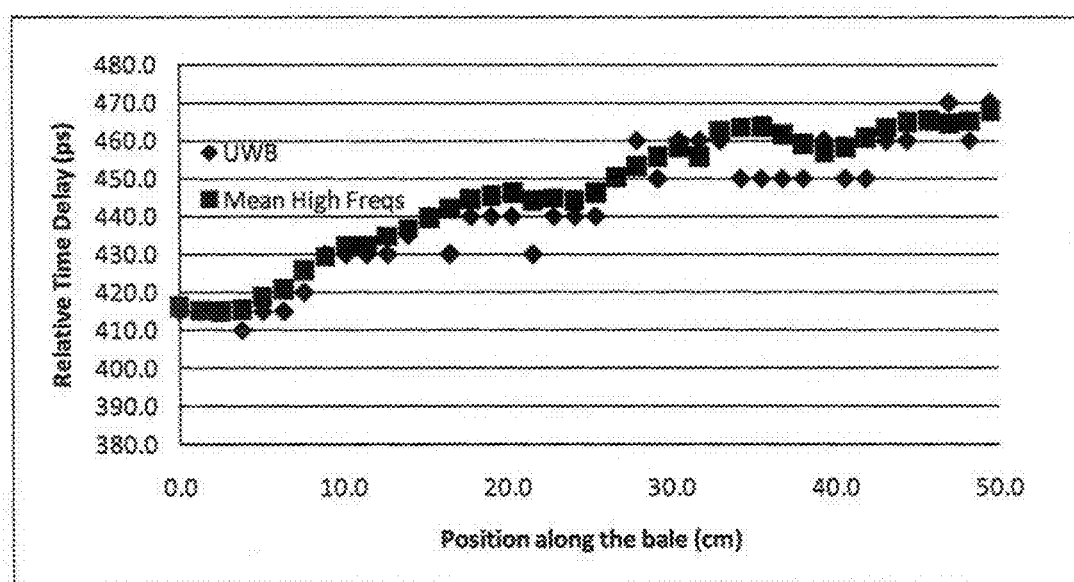
FIG. 10 illustrates a plot of the relative time delay for signals proceeding from the transmitting antenna to the receiving antenna as a function of position along the test MUT of FIG. 9, responsive to the teachings disclosed herein.

Referring now to FIG. 10, wherein the x-axis represents position along MUT 70 implemented as a cotton bale whose density increases along the bale in a uniform manner, and the y-axis represents signal time delay in picoseconds, as determined by the output of optional averaging functionality 150, it can be seen that as opposed to the plot of FIG. 9 a "straight line" result, closely tracking the bale density, is seen. Thus, the results of close proximity reflectors 75 are cancelled, and direct measurement of at least one parameter of MUT 70, substantially independent of the off-axis scattered interference, is enabled.

EXAMPLE 2

Figure 2:
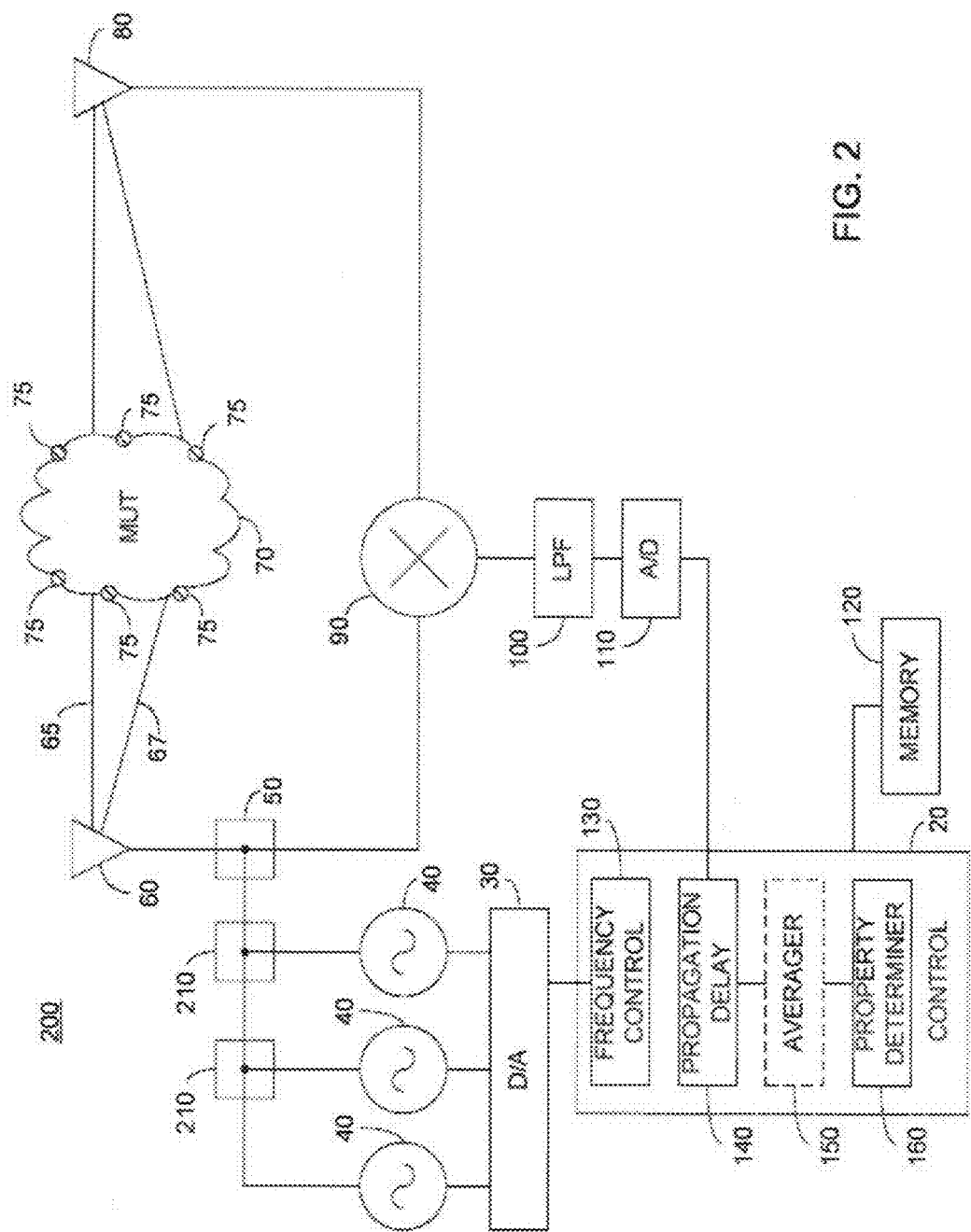
FIG. 2 illustrates a high level block diagram of an exemplary embodiment of an interrogation measurement circuit arranged to measure permittivity of an MUT subject to local proximity reflectors, the interrogation measurement circuit comprising a plurality of continuous-wave signal sources.

FIG. 2 illustrates a high level block diagram of an exemplary embodiment of a interrogation measurement circuit 200 arranged to measure permittivity of an MUT subject to local proximity reflectors, the system comprising a plurality of adjustable-frequency continuous-wave signal sources 40. Interrogation measurement circuit 200 is in all respects similar to interrogation measurement circuit 10 of FIG. 1A, with the exception that a plurality of adjustable-frequency continuous-wave signal sources 40 are provided, each controlled by frequency control functionality 130 via D/A converter 30. A plurality of combiners 210 are further provided arranged to combine the signals exiting the various adjustable-frequency continuous-wave signal sources 40 to a single mixed signal entering splitter 50.

In operation, interrogation measurement circuit 200 is in all respects similar to that of interrogation measurement circuit 10, and thus in the interest of brevity will not be further detailed, with the exception that a plurality of time varying signals at differing frequencies is simultaneously supplied. Any mixing of signals between the time varying signals are filtered by LPF 100, which may alternately be replaced by a switchable band pass filter arranged to isolate each of the plurality of mixed signals.

Three adjustable-frequency continuous-wave signal sources 40 are illustrated, however this is not meant to be limiting in any way, and more than 3 adjustable-frequency continuous-wave signal sources 40 may be provided without exceeding the scope. Preferably the provided plurality of adjustable-frequency continuous-wave signal sources 40 covers at least one half of an octave of frequency, and preferably at least one octave of frequency.

EXAMPLE 3

Figure 3A:
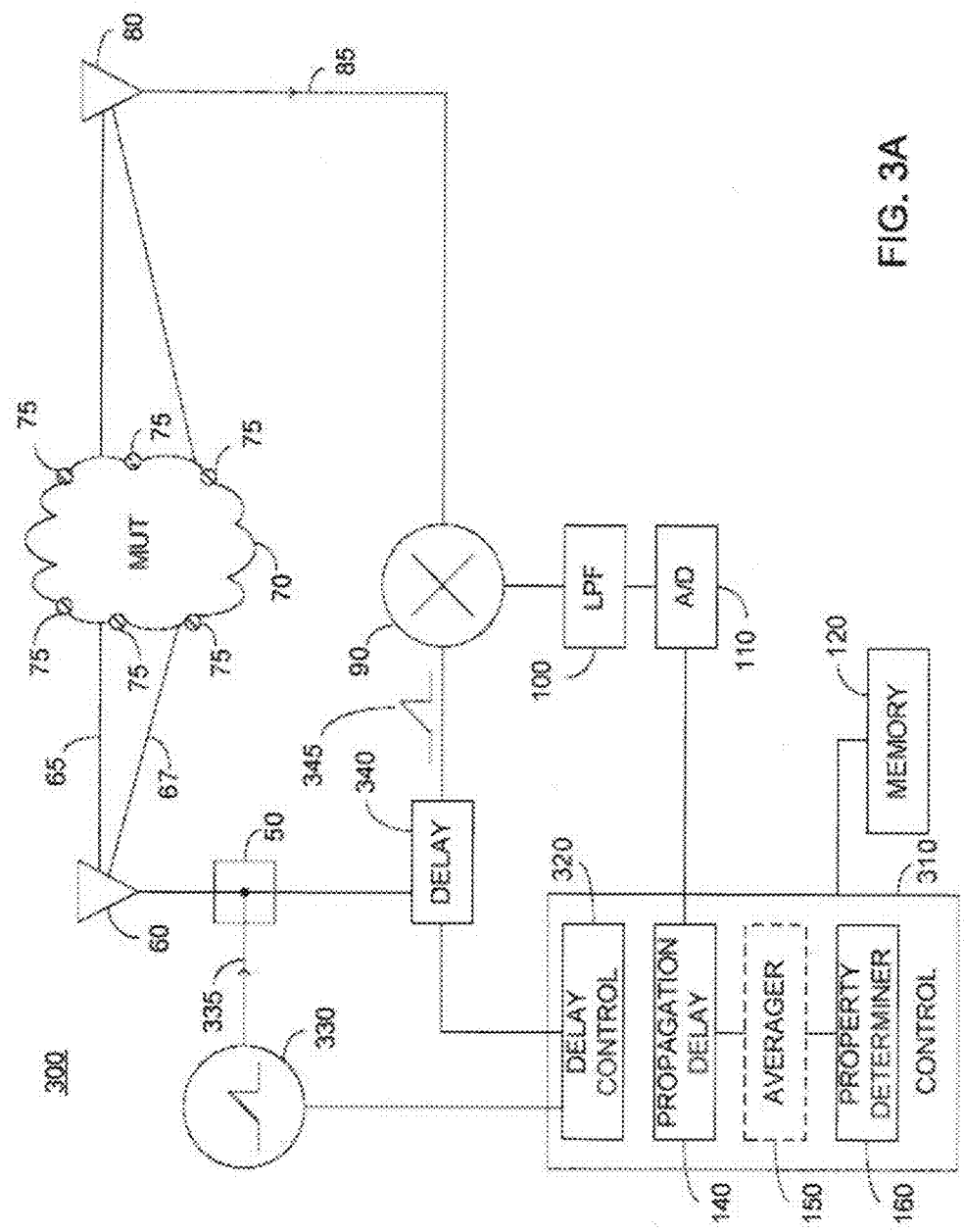
FIG. 3A illustrates a high level block diagram of an exemplary embodiment of an interrogation measurement circuit arranged to measure permittivity of an MUT subject to local proximity reflectors, the interrogation measurement circuit comprising a pulse generator and a controllable delay circuitry.

FIG. 3A illustrates a high level block diagram of an exemplary embodiment of an interrogation measurement circuit 300 arranged to measure permittivity of an MUT 70 subject to close proximity reflectors 75, the system comprising a pulse generator 330 outputting a signal 335 and a controllable delay circuitry 340 outputting a delayed signal 345. In particular, interrogation measurement circuit 300 further comprises: a control circuitry 310; a signal splitter 50; a transmitting transducer, illustrated without limitation as a transmit antenna 60; a direct path signal 65; an off-axis path signal 67; a receiving transducer, illustrated without limitation as a receive antenna 80 arranged to receive direct path signal 65 after interaction with MUT 70 and to further receive a portion of off-axis path signal 67 after interaction with MUT 70 and close proximity reflectors 75; a mixer 90; a low pass filter 100; an analog to digital converter (A/D) 110; and a memory 120. Control circuitry 310 comprises: a delay control functionality 320; a propagation delay determining functionality 140; an optional averaging functionality 150, illustrated with a broken line; and a property determining functionality 160. Control circuitry 310 may be constituted of a general purpose processor running machine readable instructions stored on memory 120, or as dedicated hardware without limitation. Each of delay control functionality 320, propagation delay determining functionality 140, optional averaging functionality 150 and property determining functionality 160 may be constituted of machine readable instructions stored on memory 120 or alternatively as dedicated hardware without limitation. Mixer 90 is preferably constituted of a frequency mixer, also known as a signal multiplier, arranged to output a mixture of signals at several frequencies, including without limitation: a signal whose frequency is the sum of the frequencies of the input signals; and a signal whose frequency is the difference between the input signals. Pulse generator 330 provides a rapid rise time signal 335 exhibiting frequency content sufficient to cover the frequency range of interest, preferably a frequency range of at least ½ octave, and preferably at least 1 octave. For a microwave implementation such suitable rise times typically range from 10's of pico-seconds, with the underlying limitation typically applied by constraint provided by the limited bandwidth of the antennas. As described above, an example performance of one such suitable wide-band antenna is illustrated in FIG. 10 which details the wide range of transmission frequencies as seen by the low standing wave-ratio "SWR", that spans across the target frequencies of interest, preferably the wide-band antenna span would encompass a minimum of at least one-half octave, and preferably at least one octave.

A first output of control circuitry 310, particularly associated with delay control functionality 320, is connected to a trigger input of pulse generator 330 and the output of pulse generator 330 is connected to the input of signal splitter 50. A first output of signal splitter 50 is connected to the input of controllable delay circuitry 340, the output of controllable delay circuitry 340 is connected to a first input of mixer 90, and a second output of signal splitter 50 is connected to the input of transmit antenna 60. A second output of control circuitry 310, particularly associated with delay control functionality 320, is connected to the control input of controllable delay circuitry 340.

Transmit antenna 60 outputs direct path signal 65 which propagates along a direct path from transmit antenna 60 to receive antenna 80 via MUT 70, and is thus received at receiving antenna 60 after interaction with MUT 70. Transmitting antenna 10 additionally outputs off-axis path signal 67 which interacts with at least one of close proximity reflectors 75 and optionally a portion of MUT 70 and at least a portion of which propagates to receive antenna 80. Receive antenna 80, comprising therein any required amplification, outputs a signal 85 representing a combination of the received direct path signal 65 after interaction with MUT 70 and off-axis path signal 67 after interaction with MUT 70 and close proximity reflectors 75. Signal 85 is connected to the second input of mixer 90.

The output of mixer 90 is connected to the input of low pass filter 100, and the output of low pass filter 100 is connected to the input of A/D converter 110. The output of A/D converter 110 is connected to the input of control circuitry 310, particularly to the input of propagation delay determining functionality 140. Propagation delay determining functionality 140 is in communication with optional averaging functionality 150, and optional averaging functionality 150 is in communication with property determining functionality 160. Control circuitry 310 is further in communication with memory 120.

Figure 3B:
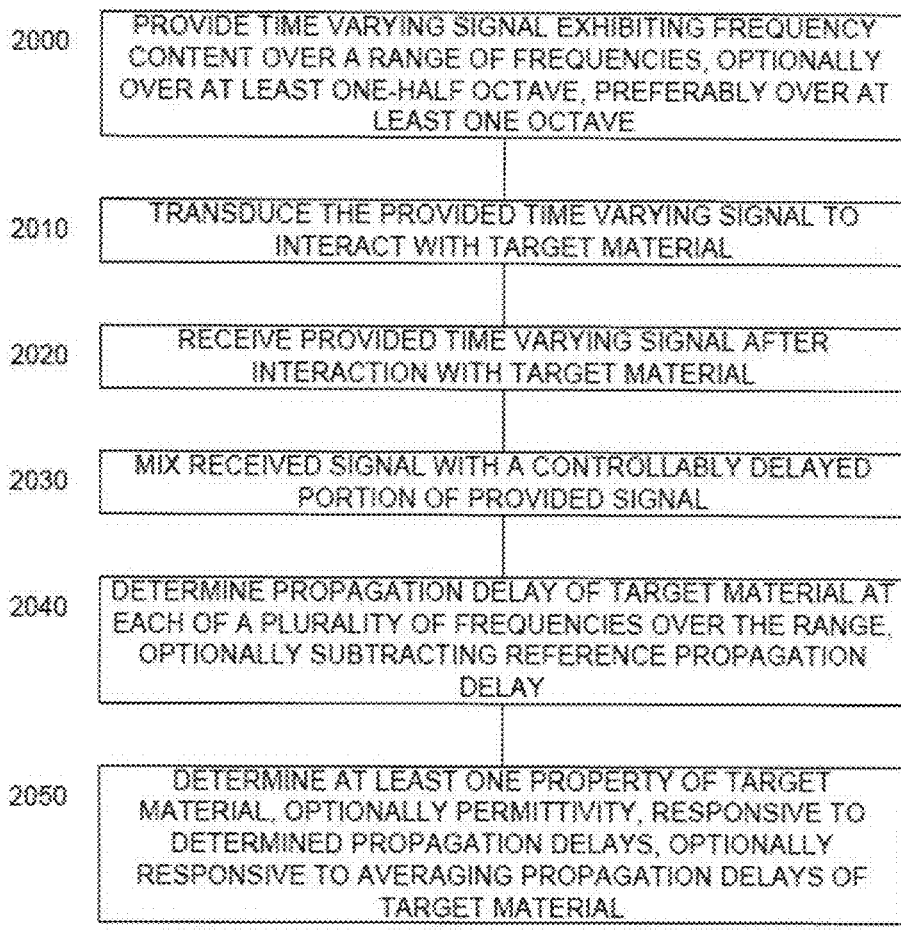
FIG. 3B illustrates a high level of flow chart of the method of operation of the interrogation measurement circuit of FIG. 3A.

FIG. 3B illustrates a high level of flow chart of the method of operation of the system of FIG. 3A. For clarity and ease of understanding FIGS. 3A-3B will be described together.

In operation, as described in stage 2000, delay control functionality 320 is arranged to periodically trigger pulse generator 330 to generate a time varying signal exhibiting frequency content over a plurality of frequencies, preferably over at least ½ octave, further preferably at least one octave.

Output signal 335 of pulse generator 330 is received by signal splitter 50, arranged to provide a first portion of signal 335 to transmit antenna 60 and to provide a second portion of signal 335 via controllable delay circuitry 340 to mixer 90 as delayed signal 345. As described at stage 2010, transmit antenna 60 transduces the received time varying signal 335 from pulse generator 330 to free space electromagnetic radiation, a first portion of which propagates as direct path signal 65 through MUT 70 to receive antenna 80 and a second portion of which propagates as off-axis path signal 67 at partially through MUT 70 to receive antenna 80. Off-axis path signal 67 is at least partially responsive to the location, size, material, and spacing of the various close proximity reflectors 75. There is no limitation to the propagation path of the free space electromagnetic radiation exiting transmit antenna 60, and a plurality of off-axis path signals 67 may exist without limitation. Additionally, off-axis path signals may exist which do not interact with MUT 70, and furthermore a portion of the electromagnetic radiation exiting transmit antenna 60 may not be received by receive antenna 80, without limitation. Transmit antenna 60 and receive antenna 80 are illustrated as being on opposing sides of MUT 70, however this is not meant to be limiting in any way, and in another embodiment transmit antenna 60 is collocated with receive antenna 80. In one particular embodiment, a single time shared antenna is provided for both transmit antenna 60 and receive antenna 80.

The time of travel of the portion of free space electromagnetic radiation propagating through MUT 70 is affected by the properties of MUT 70. In particular, the propagation velocity through MUT 70 is a function of the electrical permittivity of the constituent material of MUT 70.

As described above, and as indicated at stage 2020, receive antenna 80 captures energy from both direct path signal 65 and off-axis path signal 67 after interaction with MUT 70, and outputs the combined signal energy as signal 85. Mixer 90 receives signal 85 and, as described at stage 2030, mixes signal 85 with a controllably delayed portion of the provided time varying signal of stage 2000. In further detail, delay control functionality 320 is arranged to sweep controllable delay circuitry 340 over a pre-determined range of values, thus providing a swept, or stepped, controllably delay portion of the provided time varying signal of stage 2000 to mixer 90. It is to be noted that the received signal of stage 2020 and the provided signal of stage 2000 are of the same bandwidth, with a phase difference at least partially reflective of the permittivity of MUT 70. Mixer 90 functions to form a strong output pulse only when the phase of the delayed signal 345 matches the phase of received signal 85, thereby acting as a correlator between the internal delay set-point and the external delay created by the MUT. Low pass filter 100 is arranged to strip the high frequency portion of the output of mixer 90, thus passing only the difference signal to A/D converter 110 to be digitized which is then used to measure the propagation delay by propagation delay determining functionality 140.

Propagation delay determining functionality 140 is arranged, as described at stage 2040, to determine the propagation delay associated with MUT 70 at each of the plurality of delays of stage 2030, by correlating the delay amount of delay control functionality 320 with the received pulse from mixer 90 via A/D converter 110. In an exemplary embodiment, as illustrated in FIG. 1B, stages 2000-2030 are performed in the absence of MUT 70 and the associated close proximity reflectors 75, to determine a reference propagation delay for interrogation measurement circuit 300. The reference propagation delays are preferably stored, each associated with a relevant frequency, in memory 120, and deducted from the determined propagation delay. Deducting the reference propagation delay thus removes the influence of any internal reflections and delays. Advantageously, interrogation measurement circuit 300 directly reads the propagation delay.

Thus, the output of propagation delay determining functionality 140 exhibits the propagation delay of the signal caused by MUT 70 and further a portion of the propagation delay attributable to the various close proximity reflectors 75.

Property determining functionality 160, optionally in cooperation with optional averaging functionality 150, as described in stage 2050, is arranged to determine at least one property of MUT 70 responsive to the propagation delays output by propagation delay determining functionality 140 of stage 2040. In one embodiment, an average propagation delay of the plurality of frequencies of stage 2040 is determined, the average propagation delay representing a close approximation of the actual propagation delay of MUT 70. In particular the effects of the various close proximity reflectors 75 cancel out, and thus the average value over the range of frequencies provides a measure of the propagation delay of MUT 70 substantially independent of the off-axis scattered interference. The propagation delay of MUT 70 is a function of the permittivity, and thus permittivity may be determined directly which can then be used to infer other physical properties of interest such as moisture content, volumetric moisture, density, material composition of MUT 70 by methods taught in by; U.S. Pat. No. 4,135,131 issued Jan. 16, 1979 Larsen et al; U.S. Pat. No. 5,256,978 issued Oct. 26, 1993 to Rose; U.S. Pat. No. 5,939,888 issued Aug. 17, 1999 to Nelson; U.S. Pat. No. 6,466,168 issued Oct. 15, 2002 to McEwan; U.S. Pat. No. 7,078,913 issued Jul. 18, 2006 to Pelletier; and U.S. Pat. No. 7,254,493 issued Aug. 7, 2007 to Pelletier, the entire contents of each of which are incorporated herein by reference.

EXAMPLE 4

Figure 4:
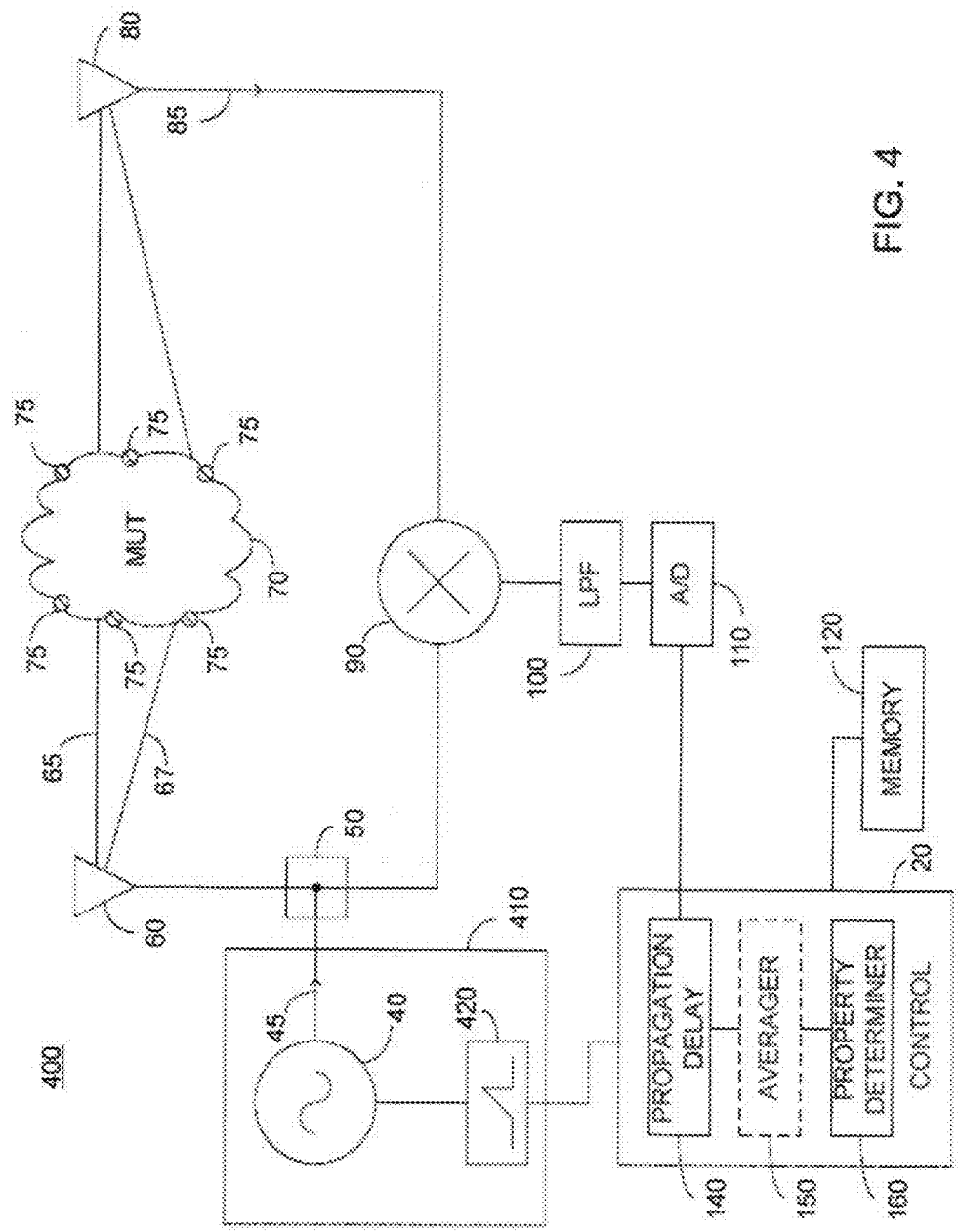
FIG. 4 illustrates a high level block diagram of an exemplary embodiment of an interrogation measurement circuit arranged to measure permittivity of an MUT subject to local proximity reflectors, the interrogation measurement circuit comprising a swept frequency signal source.

FIG. 4 illustrates a high level block diagram of an exemplary embodiment of a interrogation measurement circuit 400 arranged to measure permittivity of an MUT subject to close proximity reflectors, interrogation measurement circuit 400 comprising a swept frequency signal source 410. Interrogation measurement circuit 400 is in all respects similar to interrogation measurement circuit 10 of FIG. 1A, with the exception that swept frequency signal source signal source 410 constituted of a pulse generator 420 in communication with VCO 40 is supplied, in place of adjustable-frequency continuous-wave signal source 35. Pulse generator 420 is arranged to sweep VCO 40 across a range of frequencies, preferably over at least one-half octave, further preferably at least one octave.

Propagation delay functionality 140 in cooperation with swept frequency signal source 410 sweeps the frequency over a range of frequencies within each of a plurality of discrete frequency bands and determines the propagation delay for each of the discrete frequency bands, as known to those skilled in the art, particularly described at the above referenced U.S. Pat. No. 7,078,913.

In operation, interrogation measurement circuit 400 is in all respects similar to that of interrogation measurement circuit 10, and thus in the interest of brevity will not be further detailed, with the exception that the frequency of the transmitting signal is continuously swept over time.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof which would occur to persons skilled in the art upon reading the foregoing description and which are not in the prior art.

We claim:

1. An interrogation measurement circuit arranged to determine at least one property of a target material, the interrogation measurement circuit comprising:
   a frequency control functionality;
   at least one signal source responsive to said frequency control functionality and arranged to output a time varying signal comprising frequency content over a range of frequencies;
   a transducer in communication with said at least one signal source and arranged to output a first portion of the time varying signal so as to interact with the target material;
   a receiver arranged to receive the first portion of the time varying signal after interaction with the target material;
   a receiver arranged to receive a second portion of the time varying signal that doesn't interact with the target material thereby providing an internal reference copy of the time varying signal;
   a propagation delay calculation functionality arranged to determine the propagation delay of said received time varying signal at each of a plurality of frequencies over the range of frequencies by comparison of said first portion of time varying signal that was perturbed by the interaction with said material to the said internal reference copy of the time varying signal; and
   a property determining functionality arranged to determine at least one property of the target material responsive to the determined propagation delay at each of the plurality of frequencies.

2. The interrogation measurement circuit of any of claim 1, wherein the property is the electrical permittivity or propagation delay which is then used to estimate one or more physical properties comprising; moisture content, volumetric moisture, material density, material composition.

3. The interrogation measurement circuit of claim 2, further comprising a mixer in communication with both said at least one signal source and said receiver, said mixer arranged to mix said received first portion of the time varying signal that was perturbed by interaction with said material with said internal reference copy of time varying signal and output a low-pass filtered mixed signal, wherein mixing provides a multiplication operation of the two compared signals and said filtering removes the upper frequency created by the mixer and whereby said propagation delay calculation functionality is responsive to the filtered mixed signal.

4. The interrogation measurement circuit of claim 3, wherein said signal source comprises a swept frequency signal source, and wherein the frequency content over the range of frequencies is supplied over a span of time.

5. The interrogation measurement circuit of claim 4, wherein the range of frequencies is at least one-half of an octave.

6. The interrogation measurement circuit of any of claim 5, wherein the range of frequencies is at least one or more octaves.

7. The interrogation measurement circuit of claim 6, further comprising an averaging or best estimation functionality arranged to determine a global best estimate of propagation delay of the received time varying signal over the entire range of frequencies, said property determining functionality responsive to determined said global best estimate of propagation delay.

8. The interrogation measurement circuit of claim 7, wherein said transducer is constituted of an antenna.

9. A method of determining at least one property of a target material, the method comprising:
   providing a time varying signal or signals comprising frequency content over a range of frequencies;
   transducing said provided signal or signals so as to interact with the target material;
   receiving said provided time varying signal or signals after interaction with the target material;
   receiving a copy of said provided time varying signal or signals that doesn't interact with the target material thereby providing an unperturbed internal reference;
   determining the propagation delay associated with the target material of said received provided time varying signal or signals with respect to said internal reference copy of time varying signal or signals at each of a plurality of frequencies within the range of frequencies; and
   determining an average or best estimation of global propagation delay of said received time varying signal or signals when compared to said internal reference copy of time varying signal and repeated over the entire range of interrogated frequencies;
   determining at least one property of the target material responsive to the determined said global best estimate of propagation delay at each of the plurality of frequencies.

10. The method of claim 9, wherein the range of frequencies is at least one-half of an octave.

11. The method of claim 10, wherein the range of frequencies is at least one or more octaves.

12. The method of claim 10, further comprising:
    mixing said received time varying signal or signals with the said internal reference copy of provided time varying signal or signals to provide a low-pass filtered mixed signal and then filtering said mixed signal to remove the high frequency upper band frequencies,
    wherein said determining the propagation delay is responsive to said filtered mixed signal.

13. The method of claim 10, further comprising:
    comparing said received time varying signal or signals with the said internal reference copy of provided time varying signal or signals to provide a measure of phase between two said signals which is then converted to an estimate of propagation delay.

14. The method of claim 10, wherein the frequency content over the range of frequencies is supplied over a span of time.

15. The method of claim 10, wherein the frequency content over the range of frequencies is supplied simultaneously.

16. The method of claim 10, wherein the frequency content is swept over the range of frequencies.

17. A method of determining at least one property of a target material, the method comprising:
    providing a time varying signal or signals comprising frequency content over a range of frequencies that span at least ½ octave or more;
    transducing said provided signal or signals so as to interact with the target material;
    receiving said provided time varying signal or signals after interaction with the target material;
    receiving a copy of said provided time varying signal or signals that doesn't interact with the target material thereby providing an unperturbed internal reference;
    providing a phase or propagation-delay detector to provide a measure of the relative delay between said material perturbed time varying signal and said unperturbed internal reference;
    providing for a variable delay to allow for adjustment of how long said unperturbed internal reference takes to travel to said phase or propagation-delay detector;

adjusting said variable delay until said delayed material-unperturbed internal reference signal or signals are substantially or optimally aligned with the material perturbed time varying signal or signals, as indicated by said phase or propagation delay detector, across said range of frequencies, thereby providing a measurement of an average or best estimation of a global propagation delay;

determining at least one property of the target material responsive to the determined said global best estimate of propagation delay at each of the plurality of frequencies.

18. The method of claim 17, wherein the range of frequencies spans at least one or more octaves.

19. A method of determining at least one property of a target material, the method comprising:

providing a time varying signal or signals comprising frequency content over a range of frequencies that span at least ½ octave or more;

transducing said provided signal or signals so as to interact with the target material;

receiving said provided time varying signal or signals after interaction with the target material;

receiving a copy of said provided time varying signal or signals that doesn't interact with the target material thereby providing an unperturbed internal reference;

providing a phase or propagation-delay detector to provide a measure of the relative delay between said material perturbed time varying signal and said unperturbed internal reference;

determining the propagation delay associated with the target material of said received provided by said phase detector at each of a plurality of frequencies within the range of frequencies by adjustment; and determining an average or best estimation of global propagation delay of said received time varying signal or signals when compared to said internal reference copy of time varying signal and repeated over the entire range of interrogated frequencies;

determining at least one property of the target material responsive to the determined said global best estimate of propagation delay at each of the plurality of frequencies.

20. The method of claim 19, wherein the range of frequencies spans at least one octave.

\* \* \* \* \*